United States Patent
Clarke et al.

(10) Patent No.: US 8,298,279 B2
(45) Date of Patent: Oct. 30, 2012

(54) STENT INCLUDING A TOGGLE LOCK STRUT

(75) Inventors: Gerry Clarke, Moycullen (IE); Niall Duffy, Tuam (IE); Francis John Harewood, Bushpark (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 282 days.

(21) Appl. No.: 12/566,237

(22) Filed: Sep. 24, 2009

(65) Prior Publication Data
US 2011/0071616 A1    Mar. 24, 2011

(51) Int. Cl.
A61F 2/06    (2006.01)
A61F 2/82    (2006.01)
(52) U.S. Cl. ........................................... 623/1.15
(58) Field of Classification Search .......... 623/1.15–1.2, 623/1.3–1.35, 1.42; 606/108, 194, 198
See application file for complete search history.

(56) References Cited

U.S. PATENT DOCUMENTS

| | | | |
|---|---|---|---|
| 4,475,323 A | 10/1984 | Schwartzberg et al. | |
| 4,587,777 A | 5/1986 | Vasques et al. | |
| 4,605,140 A | 8/1986 | Koors | |
| 4,733,665 A | 3/1988 | Palmaz | |
| 4,800,882 A | 1/1989 | Gianturco | |
| 4,886,062 A | 12/1989 | Wiktor | |
| 5,133,732 A | 7/1992 | Wiktor | |
| 5,292,331 A | 3/1994 | Boneau | |
| 5,421,955 A | 6/1995 | Lau | |
| 5,496,365 A | 3/1996 | Sgro | |
| 5,545,208 A | 8/1996 | Wolff et al. | |
| 5,695,516 A * | 12/1997 | Fischell et al. ............ | 606/194 |
| 5,853,419 A | 12/1998 | Imran | |
| 5,922,020 A * | 7/1999 | Klein et al. ................ | 623/1.15 |
| 5,935,162 A | 8/1999 | Dang | |
| 5,984,963 A | 11/1999 | Ryan et al. | |
| 6,083,258 A | 7/2000 | Yadav | |
| 6,090,127 A | 7/2000 | Globerman | |
| 6,344,055 B1 | 2/2002 | Shukov | |
| 6,572,649 B2 | 6/2003 | Berry et al. | |
| 6,613,072 B2 | 9/2003 | Lau et al. | |

(Continued)

FOREIGN PATENT DOCUMENTS

EP    0887051    12/1998

(Continued)

OTHER PUBLICATIONS

Int'l Search Report for Int'l App. No. PCT/US2010/048978, Nov. 25, 2010, Medtronic Vascular Inc.

*Primary Examiner* — Elizabeth Houston

(57) ABSTRACT

A tubular stent includes cylindrical rings disposed adjacent to each other and coupled to each other by a plurality of longitudinal segments. Each cylindrical ring includes circumferentially oriented toggle lock struts. The toggle lock struts include a first arm and a second arm coupled together at an elbow. When the stent is in a compressed configuration for delivery, the toggle lock struts are bent at the elbow such that the first arm is disposed at an angle of less than 180 degrees relative to the second arm. Upon radial expansion of the stent, the toggle lock struts are unbent to a straight configuration and permitted to relax slightly beyond the straight configuration to a locked configuration such that the angle between the first arm and the second arm changes from less than 180 degrees to more than 180 degrees.

19 Claims, 8 Drawing Sheets

U.S. PATENT DOCUMENTS

| | | |
|---|---|---|
| 6,663,664 B1 | 12/2003 | Pacetti |
| 6,730,116 B1 | 5/2004 | Wolinsky et al. |
| 6,846,323 B2 | 1/2005 | Yip et al. |
| 6,945,994 B2 | 9/2005 | Austin et al. |
| 7,097,658 B2 | 8/2006 | Gktay |
| 7,141,063 B2 | 11/2006 | White et al. |
| 7,264,632 B2 | 9/2007 | Wright et al. |
| 7,704,275 B2 | 4/2010 | Schmid et al. |
| 7,722,662 B2 | 5/2010 | Steinke et al. |
| 2001/0007955 A1 | 7/2001 | Drasler et al. |
| 2002/0002397 A1 | 1/2002 | Martin et al. |
| 2002/0045930 A1 | 4/2002 | Burg et al. |
| 2003/0208260 A1 | 11/2003 | Lau et al. |
| 2004/0127971 A1 | 7/2004 | Padilla et al. |
| 2005/0015149 A1 | 1/2005 | Michelson |
| 2006/0122684 A1 | 6/2006 | Lye et al. |
| 2006/0200228 A1 | 9/2006 | Penn et al. |
| 2007/0021834 A1 | 1/2007 | Young et al. |
| 2008/0177369 A1 | 7/2008 | Allan et al. |
| 2008/0234800 A1 | 9/2008 | Clarke |

FOREIGN PATENT DOCUMENTS

| | | |
|---|---|---|
| WO | WO 02/39888 A2 | 5/2002 |
| WO | WO03/022178 A1 | 3/2003 |
| WO | WO 2006/010636 A1 | 2/2006 |

\* cited by examiner

STENT INCLUDING A TOGGLE LOCK STRUT

FIELD OF THE INVENTION

The disclosure relates generally to a tubular medical stent, and in particular, a stent including a toggle lock strut.

BACKGROUND OF THE INVENTION

Stents have gained acceptance in the medical community as a device capable of supporting body lumens, such as blood vessels, that have become weakened or are susceptible to closure. Typically, a stent is inserted into a vessel of a patient after an angioplasty procedure has been performed to partially open up the blocked/stenosed vessel thus allowing access for stent delivery and deployment. After the catheter used to perform angioplasty has been removed from the patient, a tubular stent, maintained in a small diameter delivery configuration at the distal end of a delivery catheter, is navigated through the vessels to the site of the stenosed area. Once positioned at the site of the stenosis, the stent is released from the delivery catheter and expanded radially to contact the inside surface of the vessel. The expanded stent provides a scaffold-like support structure to maintain the patency of the region of the vessel engaged by the stent, thereby promoting blood flow. Physicians may also elect to deploy a stent directly at the lesion rather than carrying out a pre-dilatation procedure. This approach requires stents that are highly deliverable i.e. have low profile and high flexibility.

These non-surgical interventional procedures often avoid the necessity of major surgical operations. However, one common problem associated with these procedures is the potential release of embolic debris into the bloodstream that can occlude distal vasculature and cause significant health problems to the patient. For example, during deployment of a stent, it is possible for the metal struts of the stent to cut into the stenosis and shear off pieces of plaque which become embolic debris that can travel downstream and lodge somewhere in the patient's vascular system. Further, pieces of plaque material can sometimes dislodge from the stenosis during a balloon angioplasty procedure and become released into the bloodstream.

Various types of endovascular stents have been proposed and used as a means for preventing restenosis. A typical stent is a tubular device capable of maintaining the lumen of the artery open. One example includes the metallic stents that have been designed and permanently implanted in arterial vessels. Metallic stents have low profile combined with high strength. Restenosis has been found to occur, however, in some cases despite the presence of the metallic stent. In addition, some implanted stents have been found to cause undesired local thrombosis. To address this, some patients receive anticoagulant and antiplatelet drugs to prevent local thrombosis or restenosis, however this prolongs the angioplasty treatment and increases its cost.

A number of non-metallic stents have been designed to address the concerns related to the use of permanently implanted metallic stents. U.S. Pat. No. 5,984,963 to Ryan et al., discloses a polymeric stent made from resorbable polymers that degrades over time in the patient. U.S. Pat. No. 5,545,208 to Wolff et al. discloses a polymeric prosthesis for insertion into a lumen to limit restenosis. The prosthesis carries restenosis-limiting drugs that are released as the prosthesis is resorbed. The use of resorbable polymers, however, has drawbacks that have limited the effectiveness of polymeric stents in solving the post-surgical problems associated with balloon angioplasty.

Polymeric stents are typically made from bioresorbable polymers. Materials and processes typically used to produce resorbable stents result in stents with low tensile strengths and low modulus, compared to metallic stents of similar dimensions. The limitations in mechanical strength of the resorbable stents can result in stent recoil after the stent has been inserted. This can lead to a reduction in luminal area and hence blood flow. In severe cases the vessel may completely re-occlude. In order to prevent the recoil, polymeric stents have been designed with thicker struts (which lead to higher profiles) or as composites to improve mechanical properties. The use of relatively thick struts makes polymeric stents stiffer and decreases their tendency to recoil, but a significant portion of the lumen of the artery can be occupied by the stent. This makes stent delivery more difficult and can cause a reduction in the area of flow through the lumen. A larger strut area also increases the level of injury to the vessel wall and this may lead to higher rates of restenosis i.e. re-occlusion of the vessel. Thus, there exists a need for a bioresorbable stent with improved mechanical strength. Similarly, a stent design that improves mechanical strength of the stent can be used with metallic stents to further reduce the profile of the stent.

BRIEF SUMMARY OF THE INVENTION

The present disclosure relates to tubular stent including a plurality of cylindrical rings disposed adjacent to each other and coupled to each other by a plurality of longitudinal segments. Each cylindrical ring includes circumferentially oriented toggle lock struts. The toggle lock struts include a first arm and a second arm coupled together at an elbow. When the stent is in a compressed configuration for delivery, the toggle lock struts are bent at the elbow such that the first arm is disposed at an angle of less than 180 degrees relative to the second arm. Upon radial expansion of the stent, the toggle lock struts are unbent to a straight configuration. When the radial expansion force is relieved the toggle lock strut will relax under the compressive force of the vessel wall until the first arm is disposed at an angle of more than 180 degrees relative to the second arm. The toggle lock strut will lock out in this position.

BRIEF DESCRIPTION OF DRAWINGS

The foregoing and other features and advantages of the disclosure will be apparent from the following description of the disclosure as illustrated in the accompanying drawings. The accompanying drawings, which are incorporated herein and form a part of the specification, further serve to explain the principles of the disclosure and to enable a person skilled in the pertinent art to make and use the invention. The drawings are not to scale.

DETAILED DESCRIPTION OF THE INVENTION

Specific embodiments of the present disclosure are now described with reference to the figures, wherein like reference numbers indicate identical or functionally similar elements.

Figure 1:
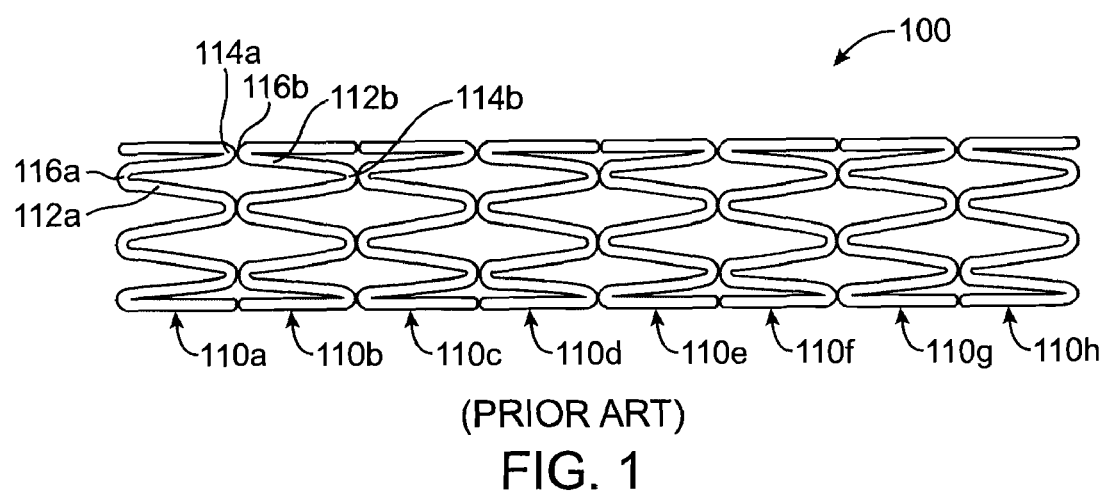
FIG. 1 is a side view of a conventional stent.

FIG. 1 is a side view of conventional stent 100 known in the art. Stent 100 includes a plurality of cylindrical rings 110a, 110b, 110c, 110d, 110e, 110f, 110g, and 110h disposed adjacent to each other. Each cylindrical ring includes a plurality of substantially straight segments 112 coupled to each other by bends 114, 116. For example, cylindrical ring 110a includes straight segments 112a coupled by bends 114a and 116b. Similarly, cylindrical ring 110b includes straight segments 112b coupled together by bends 114b and 116b. Bends 114 and 116 are peaks and valleys, respectively, of the respective cylindrical ring 110. Cylindrical rings 110 are coupled together at peaks bends 114 and 116. In the particular example shown, a peak bend 114a of cylindrical ring 110a is aligned with a valley bend 116b of adjacent cylindrical ring 110b. Bends 114a and 116b may be coupled to each other by welding or utilizing a connecting element, other ways known to those of ordinary skill in the art. For example, if stent 100 is laser or chemically etched from a tube, bends 114a and 116b may be formed as a unitary piece. Further, in a polymer stent, bends 114a and 116b may be molded as a unitary piece to couple cylindrical rings 110a and 110b together. As would be understood by one of ordinary skill in the art, all of the peak bends 114 of a cylindrical ring 110 may be coupled the adjacent valley bends 116 of an adjacent cylindrical element 110, or only some of peak bends 114 may be coupled to the valley bends 116 of an adjacent cylindrical element 110.

Figure 2:
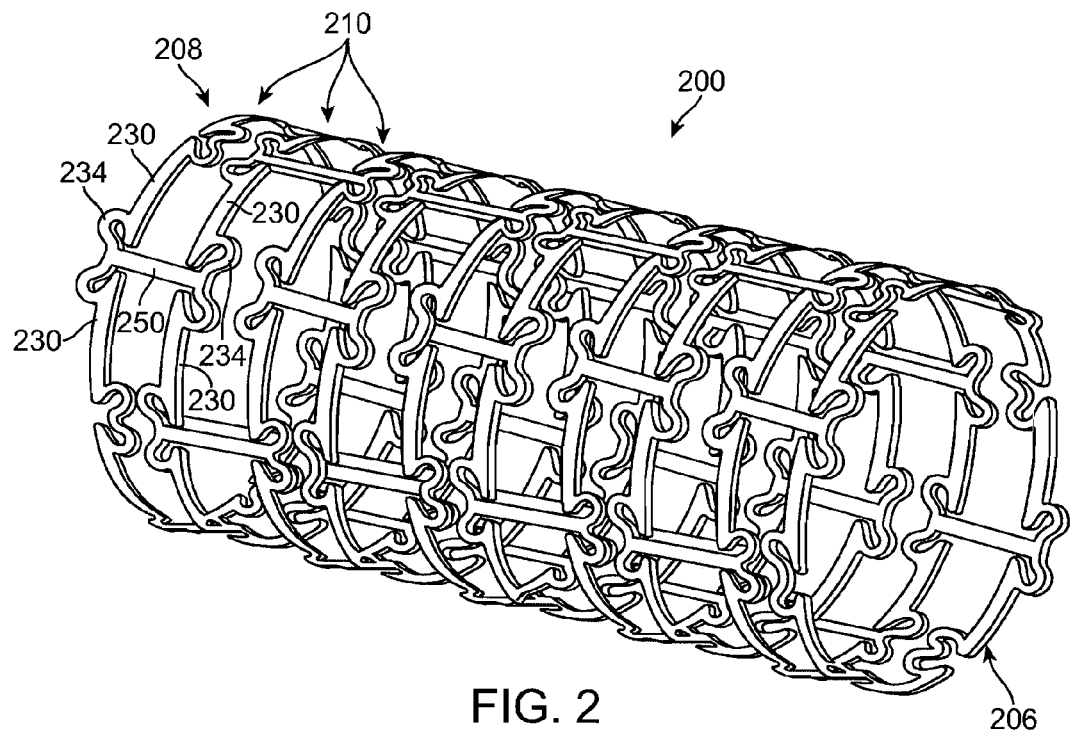
FIG. 2 is a schematic, perspective view of a stent in accordance with an embodiment hereof.
Figure 3:
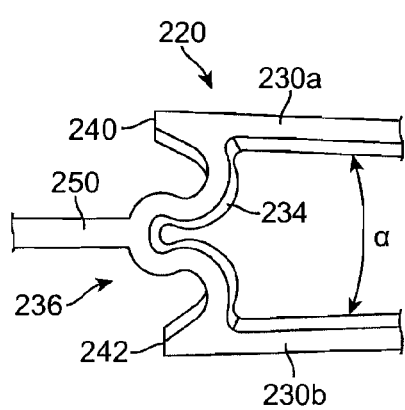
FIG. 3 is a schematic illustration of a toggle luck strut of FIG. 2 as it appears when the stent is in a radially compressed configuration.
Figure 4:
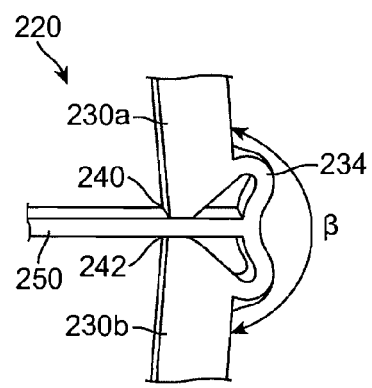
FIG. 4 is a schematic illustration of the toggle luck strut of FIG. 3 as it appears when the stent is in a locked-out configuration.

FIGS. 2-4 show a stent 200 in accordance with an embodiment hereof. FIG. 2 shows a schematic perspective view of stent 200. Stent 200 includes cylindrical elements 210. Each cylindrical element 210 includes a series of circumferential elements or arms 230 connected by generally heart-shaped elbows 234. Circumferentially adjacent elbows 234 in a cylindrical element 210 face opposite longitudinal directions. Thus, one elbow 234 in a cylindrical element 210 may face a first end 206 of stent 200 and the elbows 234 adjacent to that elbow will face a second end 208 of stent 200. Further, a longitudinal link 250 extends from each elbow 234 in the direction that the elbow faces. A link extending from an elbow in a cylindrical element 210 is coupled to (or unitary with) a link extending in the opposite directing from an elbow of an adjacent cylindrical element. Thus, stent 200 is formed by a series of circumferential arms 230 coupled to each other by elbows 234 to form a cylindrical element 210 and a series of cylindrical elements 210 coupled to each other by links 250 coupling adjacent elbows 234 to each other.

FIG. 2 is a schematic representation and thus shows adjacent arms 230 in a cylindrical element 210 generally co-linear to each other, or at an approximately 180 degree angle with respect to each other. However, as described in more detail below, stent 200 is delivered to a target location in a radially compressed configuration wherein an angle $\alpha$ between adjacent arms 230 is less than 180 degrees. As stent 200 expands, it passes through the radially expanded configuration shown in FIG. 2, wherein the angle between adjacent arms 230 is substantially 180 degrees, to a locked-out configuration wherein an angle $\beta$ between adjacent arms 230 is greater than 180 degrees.

FIGS. 3 and 4 show a portion of a toggle lock strut 220 of a cylindrical element 210 of stent 200. FIG. 3 shows the portion when stent 200 is in a radially compressed configuration and FIG. 4 shows toggle lock strut 220 when stent 200 is in the locked-out configuration. Toggle lock strut 220 includes two arms 230a, 230b coupled together by generally heart-shaped elbow 234. Longitudinal link 250 extends from elbow 234. In the radially compressed configuration shown in FIG. 3, a gap 236 is opened such that an angle $\alpha$ between arms 230a and 230b is less than 180 degrees. In some embodiments, gap 236 may open such that arms 230a and 230b may be parallel to each other (i.e., angle $\alpha$ is 0 degrees) or may even angle towards each other (i.e., angle $\alpha$ is negative). When stent 200 is in the radially compressed configuration, angle $\alpha$ may be in the range of about −45 to about 90 degrees. FIG. 4 shows toggle lock strut 220 when stent 200 is in the locked-out configuration such that the angle $\beta$ between arms 230a and 230b is greater than 180 degrees. In the radially expanded configuration gap 236 is closed such that end surfaces 240, 242 of arms 230a and 230b press against link 250, as shown in FIG. 4. In comparison to stent configurations wherein toggle lock struts 220 are unlocked such that the resistance to bending under circumferential loads relies on flexible elbows 234, this locked-out configuration with toggle lock struts 220 locking past vertical provides an increased resistance to radial compressive forces acting against stent 200. Such radial compressive forces are transmitted into circumferential loads in cylindrical elements 210 Although the embodiment of FIGS. 2-4 has been shown with generally heart shaped elbows, it would be understood by those skilled in the art that other elbows, such as those shown and described with respect to other embodiments herein, may be used with longitudinal segments extending therefrom.

Figure 5:
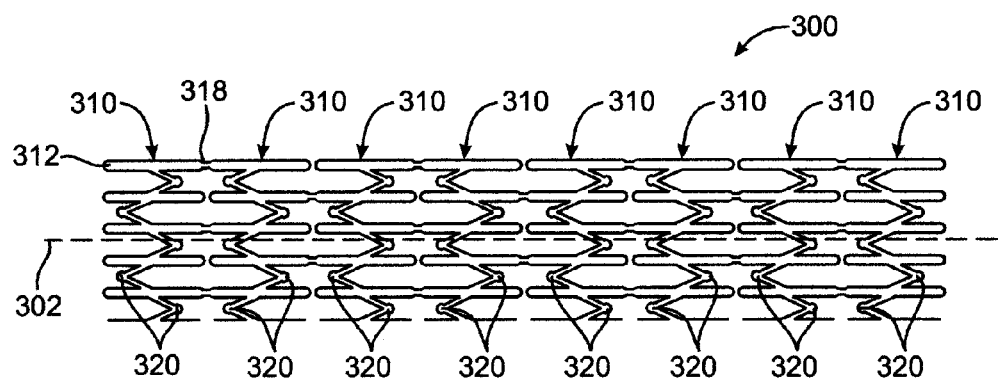
FIG. 5 is a schematic, side view of a stent in accordance with an embodiment of the present disclosure with the stent in a radially compressed configuration for delivery.

FIG. 5 is a side view of a stent 300 in accordance with another embodiment of the present disclosure. Stent 300 is shown in a compressed configuration for delivery through a body lumen, although it will be understood by those of ordinary skill in the art that the various features of stent 300 are not drawn to scale. Stent 300 is tubular and includes a longitudinal axis 302. Stent 300 includes a plurality of cylindrical rings 310. Each cylindrical ring 310 includes a plurality of longitudinal segments 312 coupled to each other by toggle lock struts 320. Toggle lock struts 320 may be coupled to longitudinal segments 312 at substantially the longitudinal center of longitudinal segments 312. In the embodiment of FIG. 5, longitudinal segments 312 are substantially straight and are substantially parallel to longitudinal axis 302. In the compressed configuration of stent 300 shown in FIG. 5, toggle lock struts 320 are bent such that adjacent longitudinal segments 312 within a cylindrical ring are close to each other. In such a condition, stent 300 has a smaller diameter for delivery through tortuous passages of the vasculature, for example.

Cylindrical rings 310 may be coupled to each other using connectors 318. Connectors 318 may be unitary pieces with longitudinal segments 312 of adjacent cylindrical rings 310, as shown. Alternatively, connectors 318 may be welds or other bonds such that selected longitudinal segments 312 of adjacent cylindrical rings 310 are welded or bonded to each other. In the embodiment shown in FIG. 5, alternating longitudinal segments 312 of a cylindrical ring 310 are connected to corresponding longitudinal segments 312 of an adjacent cylindrical ring 310. Such an arrangement improves flexibility over a similar stent with every longitudinal segment 312 coupled to a longitudinal segment 312 of the adjacent cylindrical ring 310. However, one of ordinary skill in the art would recognize that various connecting patterns may be used. For example, only two of the longitudinal segments may be connected to the adjacent cylindrical ring, or every third straight segment, etc. In the embodiment shown in FIG. 5, the connected longitudinal segments 312 are also staggered, such that the connected longitudinal segments 312 between cylindrical rings 310 are circumferentially offset from the connected longitudinal segments 312 between the next adjacent cylindrical rings 310.

Figure 6:
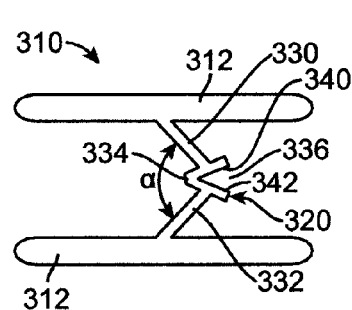
FIG. 6 is a schematic side view of a toggle lock strut of the stent of FIG. 5 as it appears when the stent is in the radially compressed configuration.
Figure 7:
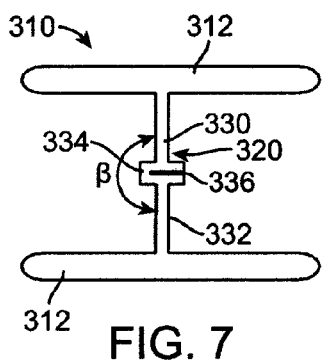
FIG. 7 is a schematic side view of the toggle lock strut of FIG. 6 as it appears when the stent is in a locked-out configuration.

FIG. 6 shows a portion of a cylindrical element 310 of stent 300 of FIG. 5, and hence shows a toggle lock strut 320, when stent 300 is in a radially compressed configuration for delivery to a target site. In the radially compressed configuration slit 336 is opened such that an angle α between first arm 330 and second arm 332 opposite slit 336 is less than 180 degrees. Angle α may be in the range of about 0 degrees to about 120 degrees. FIG. 7 shows the toggle lock strut 320 of FIG. 6 when stent 300 is in the locked-out configuration such that the angle β between first arm 330 and second arm 332 is greater than 180 degrees. In the locked-out configuration, slit 336 is closed such that surfaces 340 and 342 defining slit 336 of elbow 334 contact each other, thus locking toggle lock strut 320 to prevent elbow 334 from bending farther. The past-vertical or over-center condition of toggle lock strut 320 also is a toggle-type lock to prevent elbow 334 from reverting towards its bent shape in the compressed configuration because any compressive loads applied to the ends of a strut 320, as by inward radial force applied to stent 300 in the locked-out configuration, will only further tighten the locked-up condition of that strut. Thus, the locking feature in strut 320 prevents elbow 334 from bending in both longitudinal directions. As compared to conventional stent designs without locking circumferential struts, this locked-out configuration with toggle lock struts 320 locking past vertical provides increased hoop strength in cylindrical elements 310, which resist radial forces acting inwardly against stent 300. Thus, while stent 300 is expected to provide sufficient radial force to support a vessel wall, the elements of stent 300 may be thinner than elements of stents having different designs, i.e. without toggle lock struts, made from the same materials.

Figure 8:
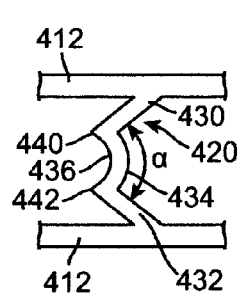
FIG. 8 is a schematic side view of a toggle lock strut as it appears when the stent is in a radially compressed configuration in accordance with another embodiment hereof.
Figure 9:
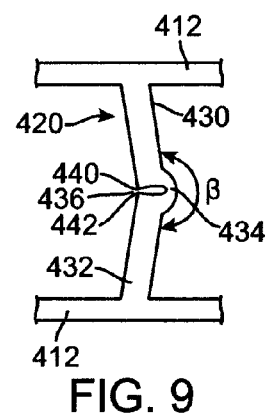
FIG. 9 is a schematic side view of the toggle lock strut of FIG. 8 as it appears when the stent is in a locked-out configuration.

FIGS. 8 and 9 show another embodiment wherein longitudinal stent segments 412 are coupled by a toggle lock strut 420. Toggle lock strut 420 shown in FIGS. 8 and 9 can be used in stents of embodiments described herein or other stents, as would be apparent to those skilled in the art. FIG. 8 shows toggle lock strut 420 when a stent is in a radially compressed configuration and FIG. 9 shows toggle lock strut 420 when the stent is in a locked-out configuration. Toggle lock strut 420 includes a first arm or portion 430 and a second arm or portion 432 coupled together by an elbow 434. Elbow 434 is similar to elbow 334 shown in FIGS. 6 and 7, although elbow 434 is generally a thin strip connecting first arm 430 and second arm 432 and is thus generally more flexible than elbow 334. Elbow 434 connects first and second arms 430, 432 along a first side of the arms, and a gap 436 between an end surface 440 of first arm 430 and an end surface 442 of second arm 432 is disposed opposite elbow 434. In the radially compressed configuration shown in FIG. 8, gap 436 is opened such that an angle α between first arm 430 and second arm 432 as measured along the first side of the arms is less than 180 degrees. Angle α with the stent in the radially compressed configuration may be in the range of about 0 degrees to about 120 degrees. FIG. 9 shows toggle lock strut 420 when the stent is in the locked-out configuration such that the angle β between first arm 430 and second arm 432 also measured along the first side of the arms is greater than 180 degrees. In the locked-out configuration gap 436 is closed such that end surfaces 440, 442 of first and second arms 430, 432 contact each other, as shown in FIG. 9. This locked-out configuration with toggle lock struts 1020 locking past vertical provides an increased resistance against compressive forces acting against the tubular stent.

Figure 10:
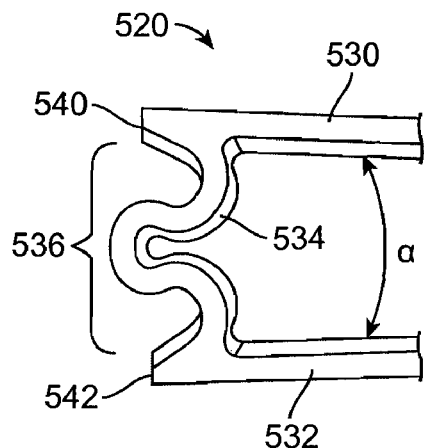
FIG. 10 is a schematic side view of a toggle lock strut as it appears when the stent is in a radially compressed configuration in accordance with another embodiment hereof.
Figure 11:
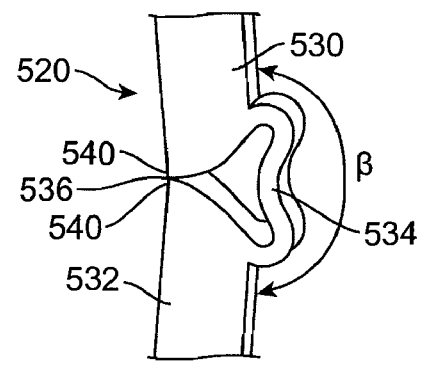
FIG. 11 is a schematic side view of the toggle lock strut of FIG. 10 as it appears when the stent is in the locked-out configuration.

FIGS. 10 and 11 show another embodiment of a toggle lock strut 520. Toggle lock strut 520 shown in FIGS. 10 and 11 can be used in stents embodiments described herein or other stents, as would be apparent to those skilled in the art. Toggle lock strut 520 shown in FIGS. 10 and 11 is similar to toggle lock strut 420 shown in FIGS. 8 and 9 except that toggle lock strut 520 includes elbow 534, which has a double hinge, a double bend or a double elbow, or may be described as generally heart-shaped when the stent is in a locked-out configuration. FIG. 10 shows toggle lock strut 520 when a stent is in a radially compressed configuration and FIG. 11 shows toggle lock strut 520 when the stent is in a locked-out configuration with toggle lock strut 520 locked past vertical. Toggle lock strut 520 includes a first arm or portion 530 and a second arm or portion 532 coupled together by a double-hinged elbow 534 comprising a pair of thin strips that are each similar to the single strip in elbow 434. A gap 536 is disposed between an end surface 540 of first arm 530 and an end surface 542 of second arm 532. In the radially compressed stent configuration shown in FIG. 10, gap 536 is opened such that an angle α between first arm 530 and second arm 532, as measured opposite gap 536, is less than 180 degrees. As discussed above with respect to FIG. 3, angle α may be in the range of about −45 to 90 degrees. FIG. 11 shows toggle lock strut 520 when the stent is in the locked-out configuration such that the angle β between first arm 530 and second arm 532, also measured opposite gap 536, is greater than 180 degrees. In the locked-out configuration, gap 536 is closed such that end surfaces 540, 542 of first and second arms 530, 532 contact each other, as shown in FIG. 11. This locked-out configuration with toggle lock struts 520 locking past vertical provides an increased resistance against radial forces acting inwardly against the cylindrical stent.

Figure 12:
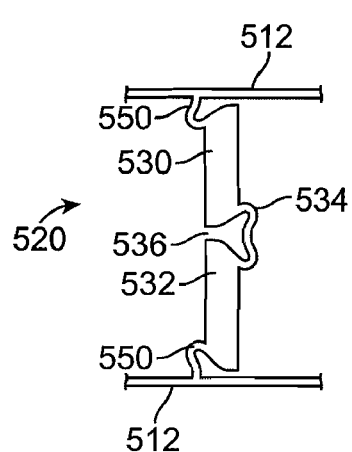
FIG. 12 is a schematic side view of the toggle lock strut of FIG. 10 including a flexible connection to the longitudinal stent segment.

FIG. 12 shows a variation of toggle lock strut 520 wherein a flexible connection 550 is provided between first arm 530 and the longitudinal stent segment 512 adjacent first arm 530. Flexible connection 550 is also provided between second arm 532 and the longitudinal stent segment 512 adjacent second arm 532, as shown. It would be understood by those skilled in the art that flexible connection 550 may be provided in any of the embodiments discussed herein. Flexible connection 550 permits strut 520 to bend at elbow 534 without deformation of arm portions 530, 532 or segments 512 while the stent is radially compressed or expanded.

Figure 13:
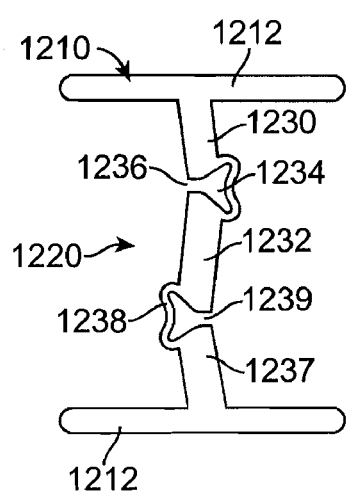
FIG. 13 is a schematic side view of a toggle lock strut in accordance with another embodiment.

FIG. 13 shows another embodiment of a toggle lock strut 1220. FIG. 13 shows a portion of a cylindrical element 1210 of a stent. Toggle lock strut 1220 is disposed between longitudinal stent segments 1212 and is similar to toggle lock strut 520. Toggle lock strut 1220 includes a first arm 1230 and a second arm 1232 coupled together by a generally heart-shaped elbow 1234. However toggle lock strut 1220 further includes a third arm 1237 coupled to the second arm 1232 by a second generally heart-shaped elbow 1238. Elbows 1234 and 1238 face opposite directions in that gap 1236 of elbow 1234 is on the opposite longitudinal side of toggle lock strut 1220 from gap 1239 of elbow 1238, as shown in FIG. 13. Although FIG. 13 shows two generally heart-shaped elbows 1234, 1238 between longitudinal segments 1212, it would be understood by those skilled in the art that the elbows of other embodiments described herein may be used.

Figure 14:
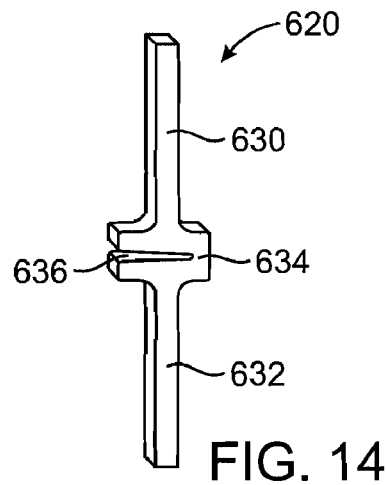
FIG. 14 is a perspective view of an embodiment of a toggle lock strut of the present disclosure.
Figure 15:
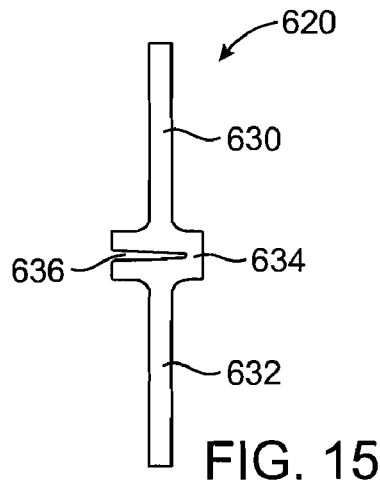
FIG. 15 is a front view of the toggle lock strut of FIG. 14.

FIGS. 14 and 15 show another embodiment of a toggle lock strut 620. As shown, toggle lock strut 620 includes two arms 630, 632 coupled together at an elbow 634, which may be considered a flexure bearing or a so-called living hinge (in plastics). Elbow 634 includes a transverse slit 636 defining a reduced thickness portion of strut 520 to enable elbow 634 to bend when a stent is in a radially compressed configurations, such as shown in FIGS. 3, 6, 8, and 10. FIGS. 14 and 15 show toggle lock strut 620 in a substantially straightened configuration, not its locked configuration. The locked configuration of strut 620 is similar to the embodiment shown in FIG. 7.

Figure 16:
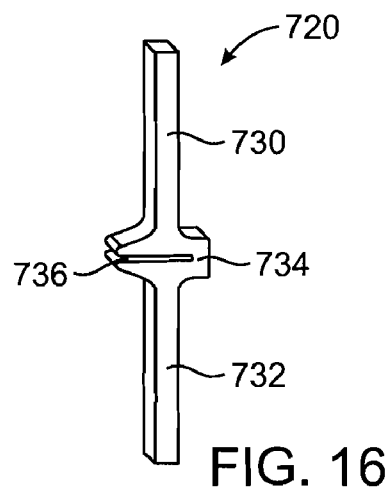
FIG. 16 is a perspective view of another embodiment of a toggle lock strut of the present disclosure.
Figure 17:
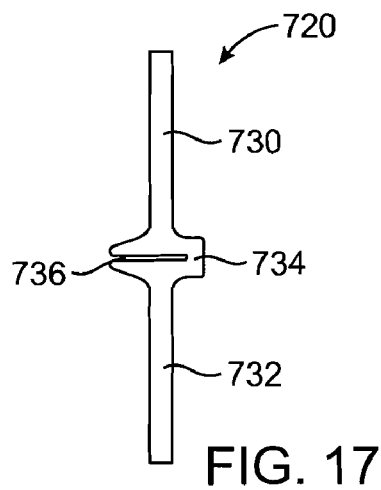
FIG. 17 is a front view of the toggle lock strut of FIG. 16.
Figure 18:
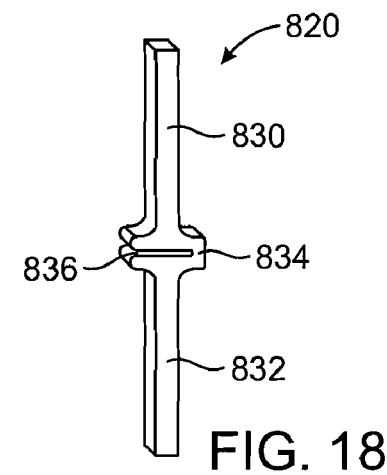
FIG. 18 is a perspective view of another embodiment of a toggle lock strut of the present disclosure.
Figure 19:
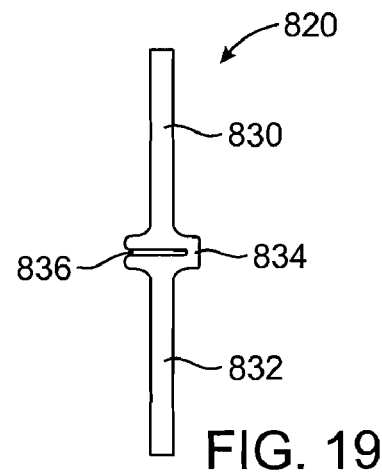
FIG. 19 is a front view of the toggle lock strut of FIG. 18.

Similarly, FIGS. 16 and 17 show another embodiment of a toggle lock strut 720 including two arms 730, 732 coupled together at an elbow 734. Elbow 734 includes a transverse slit 736 to enable elbow 734 to bend. FIGS. 18 and 19 show another embodiment of a toggle lock strut 820 including two arms 830, 832 coupled together at an elbow 834. Elbow 834 includes a transverse slit 836 to enable elbow 834 to bend. Toggle lock struts 620, 720, and 820 are similar except that the size and/or shape of elbows 634, 734, and 834 vary. As would be understood by one of ordinary skill in the art, various shapes, sizes, and structures can be used for the toggle lock struts.

Figure 20:
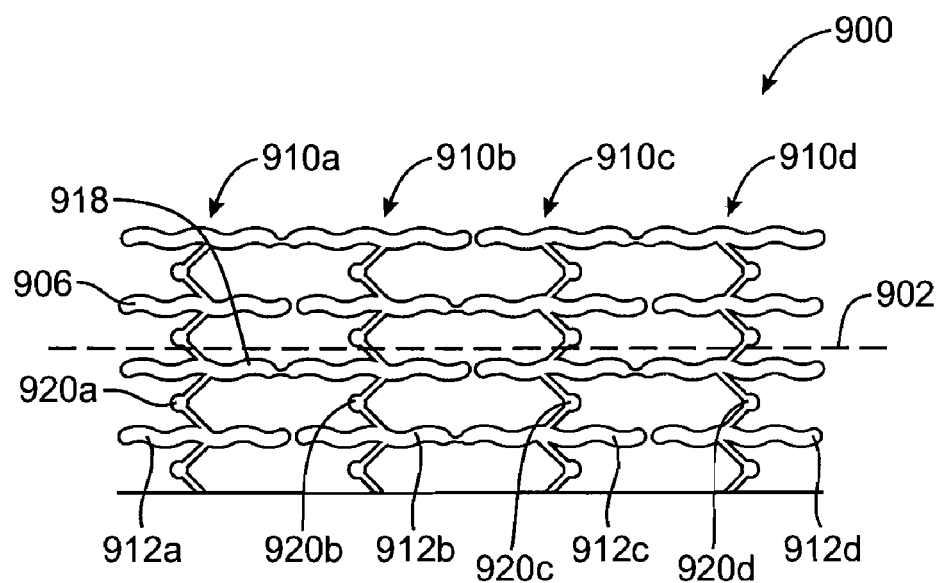
FIG. 20 is a side view of another embodiment of a stent of the present disclosure with the stent in a compressed configuration for delivery.

FIG. 20 shows an alternative embodiment of a stent 900 in accordance with the present disclosure. Stent 900 is similar to stent 300 of FIG. 5, except that longitudinal segments 912a, 912b, 912c, and 912d of cylindrical rings 910a, 910b, 910c, and 910d are curved or wave-shaped along the length of the segments. In this embodiment, an axis 906 through one of longitudinal segments 912 is parallel to longitudinal axis 902 of stent 900. As in FIG. 5, toggle lock struts 920a, 920b, 920c, and 920d connect longitudinal segments 912a, 912b, 912c, and 912d, respectively, and may be connected to generally the longitudinal center of the respective longitudinal segments. FIG. 20 shows stent 900 in the compressed configuration. Upon expansion, toggle lock struts 920 of stent 900 straighten similar to struts 620, 720 and 820 as shown in FIGS. 14-19. Furthermore, toggle lock struts 920 of stent 900 can transform over-center or past vertical from the straight configuration to become locked similar to toggle lock strut 320 as shown in FIG. 7.

Figure 21:
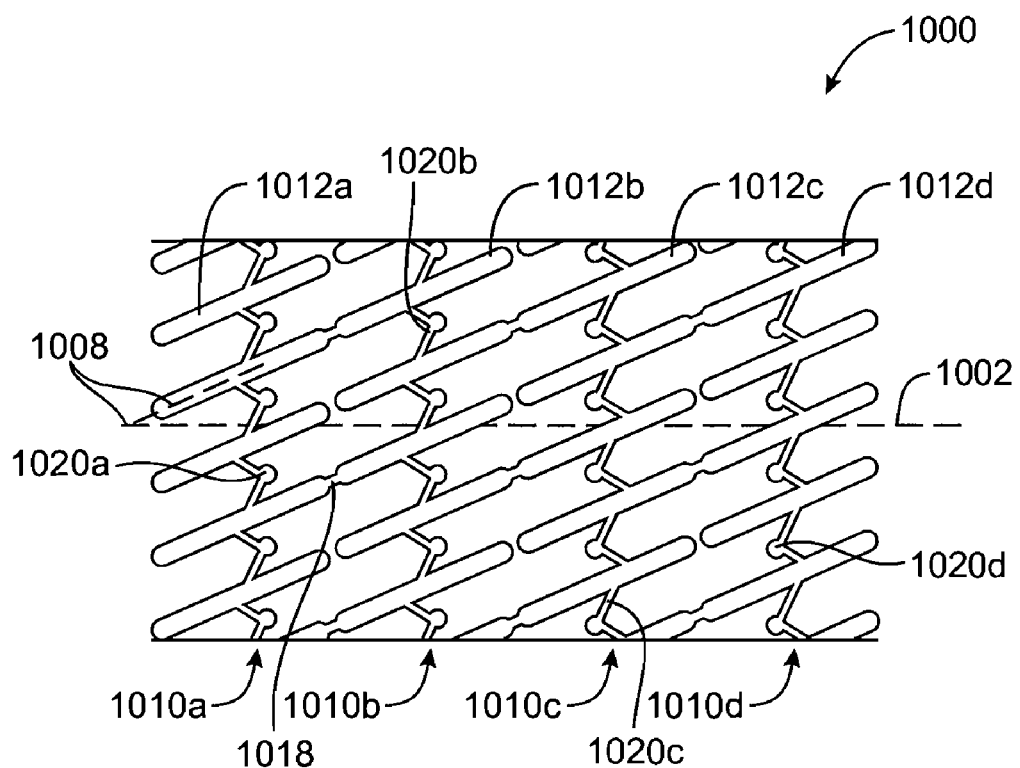
FIG. 21 is a side view of another embodiment of a stent of the present disclosure with the stent in a compressed configuration for delivery.

FIG. 21 shows an alternative embodiment of a stent 1000 in accordance with the present disclosure. Stent 1000 is similar to stent 300 of FIG. 5, except that longitudinal segments 1012a, 1012b, 1012c, and 1012d of cylindrical rings 1010a, 1010b, 1010c, and 1010d are disposed at an angle 1008 to longitudinal axis 1002 of stent 1000. As in FIGS. 5-7, toggle lock struts 1020a, 1020b, 1020c, and 1020d connect longitudinal segments 1012a, 1012b, 1012c, and 1012d, respectively, and may be connected to generally the longitudinal center of the respective longitudinal segments. FIG. 21 shows stent 1000 in the compressed configuration. Upon expansion, toggle lock struts 1020 of stent 1000 will transform through a straightened configuration to a locked, over-center configuration similar to toggle lock struts 320 as shown in FIG. 7.

As would be understood by one of ordinary skill in the art, several variations of the longitudinal segments may be utilized, and FIGS. 5, 20, and 21 merely provide some examples. Further, different segment variations may be used in the same stent.

The stents described herein may be made of materials commonly used for stents, such as stainless steel, MP35N® and MP20N and L605 cobalt alloys, nickel titanium alloys such as nitinol, tantalum, platinum-iridium alloy, gold, magnesium, or combinations thereof. MP35N is a registered trademark of SPS Technologies, Inc., Jenkintown, Pa. for alloys of cobalt, nickel, chromium and molybdenum. MP35N consists of 35% cobalt, 35% nickel, 20% chromium, and 10% molybdenum. MP20N is a trade name of SPS Technologies, Inc. and consists of 50% cobalt, 20% nickel, 20% chromium, and 10% molybdenum. The stents described herein made of a metallic material may be made in by process known to those of ordinary skill in the art. For example, and not by limitation, a thin-walled, small diameter metallic tube is cut to produce the desired stent pattern, using methods such as laser cutting or chemical etching. The cut stent may then be descaled, polished, cleaned and rinsed. Some examples of methods of forming stents and structures for stents are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,935,162 to Dang, U.S. Pat. No. 6,090,127 to Globerman, and U.S. Pat. No. 6,730,116 to Wolinsky et al., each of which is incorporated by reference herein in its entirety.

Further, the stents described herein may be made of a polymer material suitable for use in a human body. Examples of polymers include but are not limited to, poly-a-hydroxy acid esters such as, polylactic acid (PLLA or DLPLA), polyglycolic acid, polylactic-co-glycolic acid (PLGA), polylactic acid-co-caprolactone; poly (block-ethylene oxide-block-lactide-co-glycolide) polymers (PEO-block-PLGA and PEO-block-PLGA-block-PEO); polyethylene glycol and polyethylene oxide, poly (block-ethylene oxide-block-propylene oxide-block-ethylene oxide); polyvinyl pyrrolidone; polyorthoesters; polysaccharides and polysaccharide derivatives such as polyhyaluronic acid, poly (glucose), polyalginic acid, chitin, chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like. The stents described herein made of a polymeric material may be formed by injection molding, spraying, or casting, or any other methods known to one of ordinary skill in the art.

The stents described herein can be coated with a therapeutic substance. Further, the stents can be formed with recesses or openings in which to deposit such therapeutic substances. Examples of therapeutic substances include, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., TAXOTERE® from Aventis S. A., Frankfurt, Germany), methotrexate, azathioprine, vincristine, vinblastine, fluorouracil, doxorubicin hydrochloride (e.g., ADRIAMYCINO from Pharmacia & Upjohn, Peapack N.J.), and mitomycin (e.g., MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (Biogen, Inc., Cambridge, Mass.). Examples of such cytostatic or antiproliferative agents include angiopeptin, angiotensin converting enzyme inhibitors such as captopril (e.g., CAPOTEN® and CAPOZIDE® from Bristol-Myers Squibb Co., Stamford, Conn.), cilazapril or lisinopril (e.g., PRINIVIL® and PRINZIDE® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone. In other examples, the therapeutic substance is a radioactive isotope for implantable device usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$). While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

Deployment of a stent in accordance with embodiments hereof may be accomplished by tracking a catheter-based delivery system through the vasculature of the patient until the stent is located within a target vessel. The catheter-based delivery system may include an inner shaft having the stent mounted at a distal end thereof, and a retractable outer sheath that covers and constrains the stent in a radially compressed configuration while the delivery system is tracked through a vessel to the delivery site. For example, the catheter-based delivery system may be the system described in U.S. Pat. No. 7,264,632 to Wright et al., which is incorporated by reference herein in its entirety, or other such similar delivery systems that are well known in the art. The catheter-based delivery system may, alternatively, be a balloon catheter system wherein the stent is mounted over the balloon, as known to those skilled in the art. In this example, when the delivery system reaches the delivery site, the balloon is expanded to expand the stent from the radially compressed configuration to the radially expanded configuration. The stent may alternatively be partially self-expanded and then further expanded by a balloon to ensure that the toggle lock struts are expanded beyond vertical to lock the toggle lock struts, as explained above.

Figure 22:
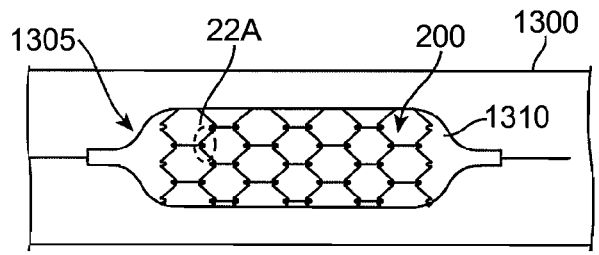
FIGS. 22-25A are schematic views of an embodiment of a method for deploying a stent in accordance with the present disclosure showing the stent from a compressed configuration to a locked-out configuration.
Figure 22A:
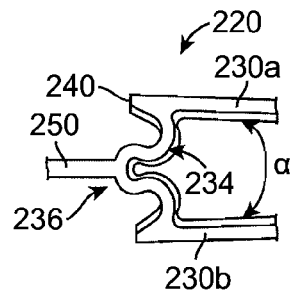

FIGS. 22-25A show an embodiment of a method for deploying a stent from a compressed configuration to a locked-out configuration. The embodiment of FIGS. 22-25A shows the stent 200 of FIGS. 2-4. It would be understood by those skilled in the art that other stents described herein could be used. In this embodiment, stent 200 is mounted on a balloon 1310 of a balloon catheter 1305 and delivered to a target location within a vessel 1300, such as a coronary artery. Balloon catheters and their delivery to a target location are well known to those skilled in the art. During delivery, stent 200 is in the radially compressed configuration. In the radially compressed configuration, as can be seen in FIG. 22A, gap 236 of each toggle lock strut 220 is open such that arms 230a, 230b are disposed at an angle α less than 180 degrees to each other. FIG. 22A depicts a portion of stent 200 in the radially compressed configuration described with respect to FIG. 3. It would be understood by those skilled in the art that other features of balloon catheter 1305 are not shown or described. In a non-limiting example, a sheath (not shown) can be provided over stent 200.

Figure 23:
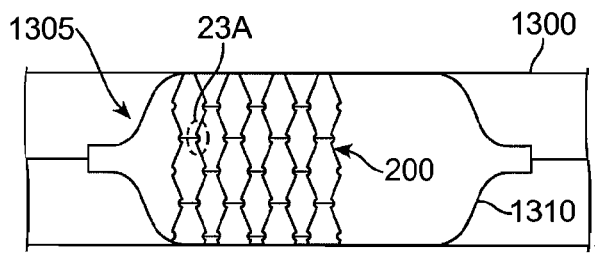
Figure 23A:
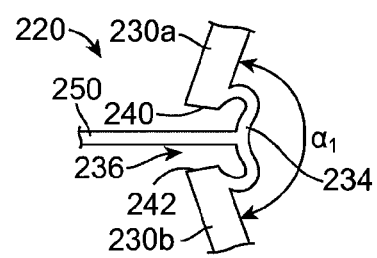
Figure 24:
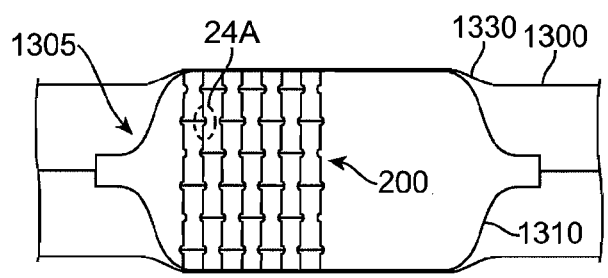
Figure 24A:
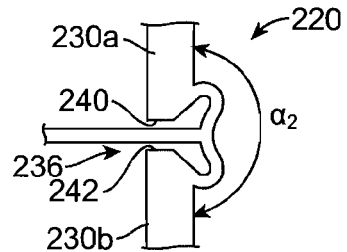

After balloon catheter 1305 is at the target location, balloon 1310 may be inflated, as shown schematically in FIG. 23. As balloon 1310 inflates, it expands stent 200 radially. As stent 200 expands, gap 236 begins to close and arms 230a, 230b begin to align with each other, thereby straightening toggle lock strut 220 such that angle $α_1$ approaches 180 degrees, as shown in FIG. 23A. As angle $α_1$ approaches 180 degrees, stent 200 contacts the wall of vessel 1300. Balloon 1310 continues to expand, slightly dilating vessel wall 1300, as shown in FIG. 24 at 1330. FIG. 24 shows stent 200 at maximum radial expansion, with arms 230a, 230b straightened such that angle $α_2$ is about 180 degrees, as shown in FIG. 24A. At this time in the expansion, gap 236 of toggle lock strut 220 is almost closed.

Figure 25:
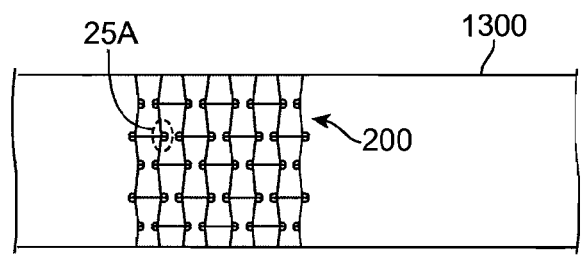
Figure 25A:
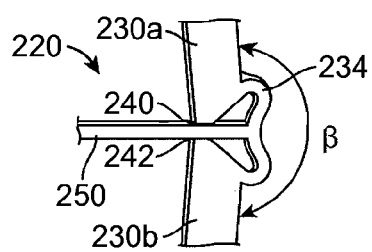

Balloon 1310 is then deflated, and stent 200 relaxes into its locked-out configuration, as shown in FIG. 25. As shown in FIG. 25A (and FIG. 4), gap 236 is closed and arms 230a, 230b press against link 250. Further, angle β is greater than 180 degrees.

Figure 26:
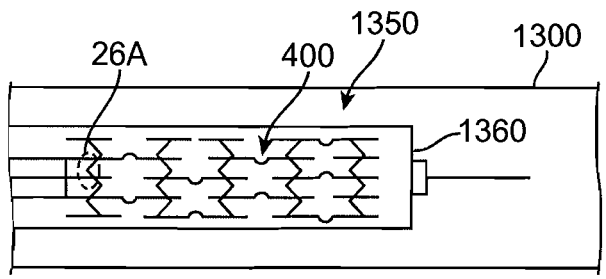
FIGS. 26-29A are schematic views of an embodiment of a method for deploying a stent in accordance with the present disclosure showing the stent from a compressed configuration to a locked-out configuration.
Figure 26A:
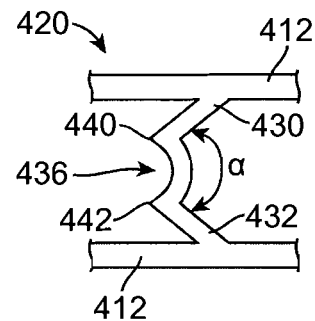

FIGS. 26-29A show schematically a method of deploying a stent from a compressed configuration to a locked-out configuration in accordance with another embodiment of the disclosure. In the embodiment of FIGS. 26-29A, the stent is self-expanding. As known to those skilled in the art, self-expanding stents are generally pre-set into their deployed configuration, radially compressed and captured for delivery, and then released back to their pre-set configuration. In the present embodiment, a stent 400 with toggle lock struts 420 as shown in FIGS. 6-7 is shown, but any stent design including toggle lock struts can be used. In this embodiment, stent 400 is pre-set to the locked out configuration shown in FIG. 29. In order to deliver stent 400 to the target location within the vessel 1300, stent 400 is radially compressed and disposed within a sheath 1360 or similar device of a delivery catheter 1350, as shown in FIG. 26. In the compressed configuration, gap 436 of toggle lock strut 420 is open such that arms 430, 432 are disposed at angle α less than 180 degrees with respect to each other, as shown in FIG. 26A.

Figure 27:
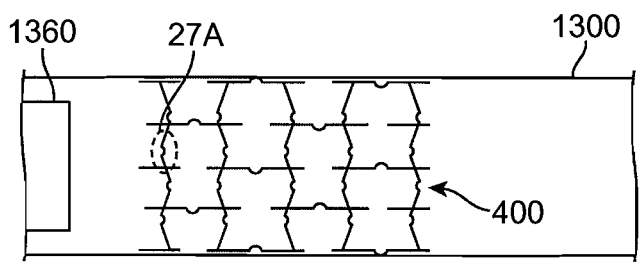
Figure 27A:
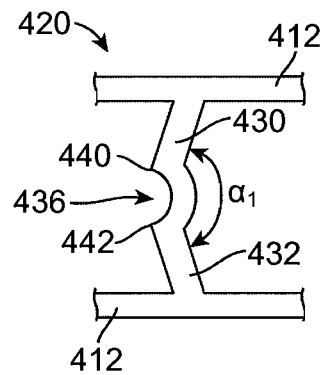

After delivery catheter 1350 has reached the target location, sheath 1360 is withdrawn proximally to release stent 400. As stent 400 is released, stent 400 attempts to return to its pre-set configuration which, in this embodiment, is the locked-out configuration. As stent 400 transforms towards the locked out configuration, the wall of vessel 1300 prevents it from fully expanding in the radial direction. Stent 400 is thus in the configuration shown in FIGS. 27 and 27A, wherein stent 400 has expanded such that arms 430, 432 have moved away from each other such that angle $\alpha_1$ is still less than 180 degrees, but is approaching 180 degrees.

Figure 28:
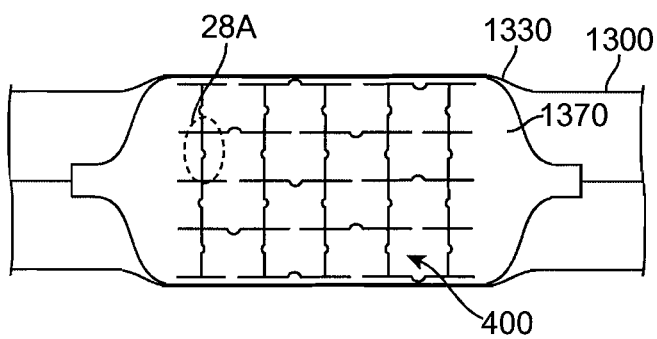
Figure 28A:
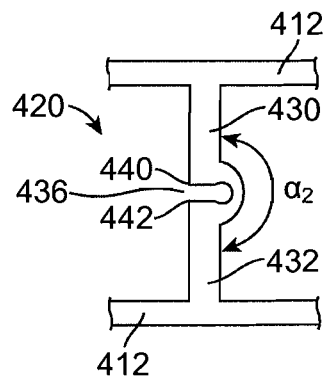

A balloon 1370 is then inflated to expand tubular stent 400 to overcome radial compressive force from the vessel wall such that stent 400 can be expanded to its maximum radial expansion, as shown in FIGS. 28 and 28A. Balloon 1370 may be provided with catheter 1350 or may be separately inserted after sheath 1360 is withdrawn. As balloon 1370 expands, it dilates the vessel wall, as shown in FIG. 28. FIG. 28 shows stent 400 at maximum radial expansion, with arms 430, 432 aligned with each other such that toggle lock strut 420 is straightened and angle $\alpha_2$ is about 180 degrees, as shown in FIG. 28A. At this time in the expansion, gap 436 of toggle lock strut 420 is almost closed.

Figure 29:
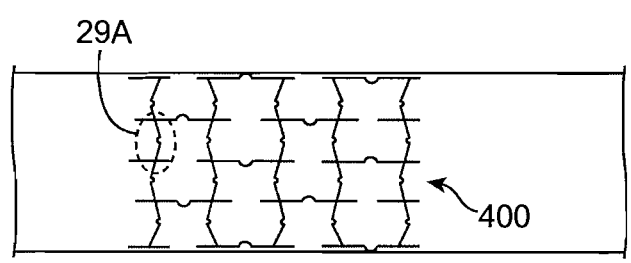
Figure 29A:
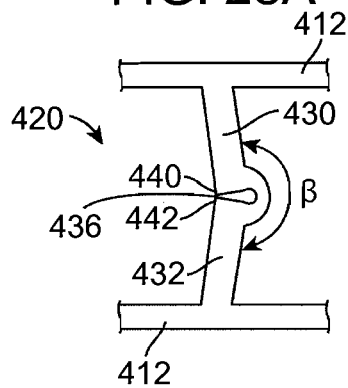

As balloon 1370 is deflated, stent 400 seeks it pre-set configuration, which is the locked-out configuration shown in FIG. 29. As shown in FIG. 29A (and FIG. 7), when stent 400 is in the locked-out configuration, gap 436 is closed and end surfaces 440, 442 of arms 430, 432 press against each other. Further, toggle lock strut 420 has toggled or transformed over-center such that angle β is greater than 180 degrees.

While various embodiments of the present disclosure have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present disclosure should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent comprising:
a plurality of cylindrical rings coupled together to form a tube having a longitudinal axis and a circumference, wherein the tube includes a radially compressed configuration having a first diameter and a locked-out configuration having a second diameter larger than the first diameter, wherein at least one cylindrical ring is formed at least partially by:
a first arm,
a second arm,
and an elbow coupling the first arm and the second arm, wherein the combination of the first arm, the second arm, and the elbow extends generally circumferentially when the tube is in the locked-out configuration;
wherein, in the radially compressed configuration, an angle between the first arm and the second arm is less than 180 degrees and a gap is formed between a first end of the first arm coupled to the elbow and a second end of the second arm coupled to the elbow, and wherein, in the locked-out configuration, the angle is more than 180 degrees and the gap is closed to resist radial compressive forces acting on the stent.

2. The stent of claim 1, further comprising segments extending generally longitudinally and coupling the cylindrical rings to each other.

3. The stent of claim 2, wherein the segments extend from the elbow.

4. The stent of claim 3, wherein when the gap is closed, the first end of the first arm and the second end of the second arm each contacts the segment extending from the elbow coupling the first arm and the second arm.

5. The stent of claim 2, wherein the first arm, second arm, elbow, and segments extending generally longitudinally are made from a polymeric material.

6. The stent of claim 2, wherein first arm, second arm, elbow, and segments extending generally longitudinally are made from a metal material.

7. The stent of claim 1, wherein the elbow is substantially heart shaped.

8. The stent of claim 1, wherein the first arm, second arm, and elbow are made from a polymeric material.

9. The stent of claim 1, wherein when the gap is closed, the first end of the first arm contacts the second end of the second arm.

10. A stent having a radially compressed configuration and a locked-out configuration, the stent comprising:
a first cylindrical ring including a first plurality of arms extending generally circumferentially when the stent is in the locked-out configuration, the first plurality of arms being connected together by a first plurality of elbows such that adjacent arms on the first plurality of arms are coupled by a respective elbow of the first plurality of elbows; and
a second cylindrical ring coupled to the first cylindrical ring to form a tube having a longitudinal axis, the second ring including a second plurality of arms extending generally circumferentially when the stent is in the locked-out configuration, the second plurality of arms being connected together by a second plurality of elbows such that adjacent arms on the second plurality of arms are coupled by a respective elbow of the second plurality of elbows;
wherein when the stent is in the radially compressed configuration, adjacent arms in the first plurality of arms form an angle of less than 180 degrees and a gap is formed between ends of the adjacent arms coupled to the respective elbow, and when the stent is in the locked-out configuration, adjacent arms in the first plurality of arms together extend generally circumferentially and form an angle greater than 180 degrees and the gap is closed such that the closed gap resists radial compressive forces acting on the stent.

11. The stent of claim 10, wherein when the stent is in the radially compressed configuration, adjacent arms in the second plurality of arms form an angle of less than 180 degrees and a gap is formed between ends of the adjacent arms coupled to the respective elbow, and when the stent is in the locked-out configuration, adjacent arms in the second plurality of arms form an angle greater than 180 degrees and the gap is closed.

12. The stent of claim 10, further comprising a segment extending generally longitudinally and coupling the first cylindrical ring and the second cylindrical ring.

13. The stent of claim 12, wherein the segment extends from an elbow in the first plurality of elbows to an elbow in the second plurality of elbows.

14. The stent of claim 13, wherein when the gap is closed, the ends of adjacent arms contact the segment extending from the elbow between the adjacent arms.

15. The stent of claim 12, wherein the elbows are substantially heart-shaped.

16. The stent of claim 10, wherein the stent comprises additional cylindrical rings.

17. The stent of claim 16, wherein the stent comprises ten cylindrical rings.

18. The stent of claim 10, wherein each cylindrical ring comprises eight arms and eight elbows.

19. The stent of claim 10, wherein when the gap is closed, the ends of adjacent arms contact each other.

\* \* \* \* \*